United States Patent [19]

Hukuba

[11] Patent Number: 5,115,533
[45] Date of Patent: May 26, 1992

[54] TOOTHBRUSH WITH VOLTAGE TESTER

[76] Inventor: Hiroshi Hukuba, No. 914-1, Nazukari, Nagareyama, Chiba, Japan

[21] Appl. No.: 578,281

[22] Filed: Sep. 6, 1990

[30] Foreign Application Priority Data

Sep. 12, 1989 [JP] Japan .................................. 1-236491

[51] Int. Cl.$^5$ ...................... A46B 17/02; A61N 1/26
[52] U.S. Cl. ..................... 15/105; 15/143 R; 15/167.1; 15/176.1; 128/393; 128/787; 128/800; 128/801; 324/133; 604/20
[58] Field of Search ............... 15/105, 167.1, 176.1, 15/143 R; 128/24.5, 62 A, 393, 419 R, 787, 799-801; 604/20; 132/311; 433/32, 141, 216; 324/133, 437

[56] References Cited

U.S. PATENT DOCUMENTS

| 407,115 | 7/1889 | Pratt | 128/799 X |
|---|---|---|---|
| 2,834,344 | 5/1958 | Kanai | 128/393 X |
| 3,412,731 | 11/1968 | Reynolds | 15/167.1 X |
| 3,478,741 | 11/1969 | Simor | 15/167.1 X |
| 3,520,297 | 7/1970 | Bechtold | 15/167.1 |
| 3,571,708 | 3/1971 | Hurt | 324/133 |
| 4,253,212 | 3/1981 | Fujita | 15/167.1 |
| 4,665,921 | 5/1987 | Teranishi | 128/800 X |
| 4,691,718 | 9/1987 | Sakuma et al. | 128/393 X |
| 4,944,296 | 7/1990 | Suyama | 128/393 |
| 4,969,868 | 11/1990 | Wang | 128/787 X |

FOREIGN PATENT DOCUMENTS

| 207678 | 1/1987 | European Pat. Off. | 324/133 |
|---|---|---|---|
| 357852 | 3/1990 | European Pat. Off. | 15/167.1 |
| 3724476 | 1/1989 | Fed. Rep. of Germany | 15/167.1 |
| 2491309 | 4/1982 | France | 15/167.1 |
| 2595221 | 9/1987 | France | 15/167.1 |
| 466215 | 1/1969 | Switzerland . | |
| 660120 | 3/1987 | Switzerland | 15/167.1 |

Primary Examiner—Harvey C. Hornsby
Assistant Examiner—C. Cooley
Attorney, Agent, or Firm—Sixbey, Friedman, Leedom & Ferguson

[57] ABSTRACT

An electronic toothbrush including a head portion at one end which is studded with bristles, a grip portion in the middle which contains a battery, and a voltage tester at the other end which is separable from the grip portion and has a tester body with coupling means associated with the grip portion for separably coupling the tester body with the grip portion. The grip portion has a first electrically conductive member which is adapted to be touched by a user and is electrically connected to one pole of the battery, and a second electrically conductive member which is adapted to be electrically connected to the bristles and is electrically connected to the other pole. The tester has a light emitting member mounted inside the tester body and visible from outside the tester body, and a pair of electrical conductors extending from the light emitting member and being exposed at least partially from the tester body. When the pair of electrical conductors of the tester separated from the grip portion contact the first and second conductive members of the grip portion, the emission of light by the light emitting member is determined by the condition of the battery.

18 Claims, 11 Drawing Sheets

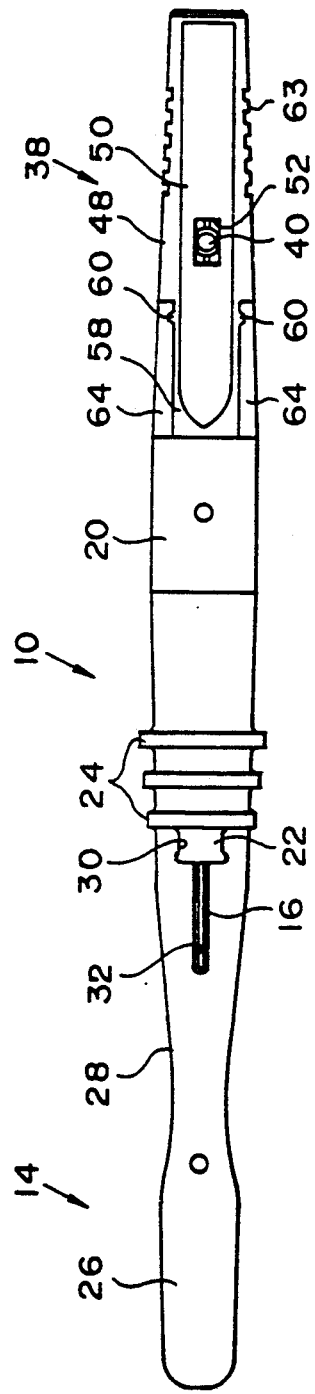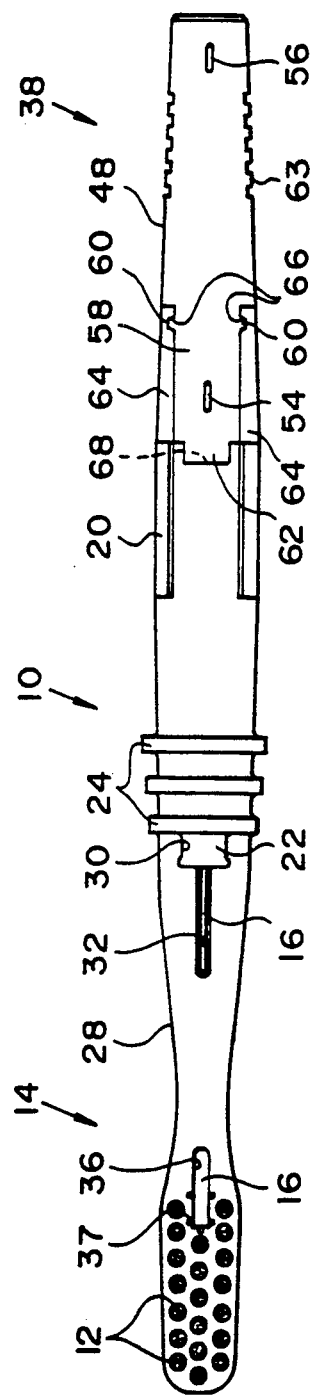

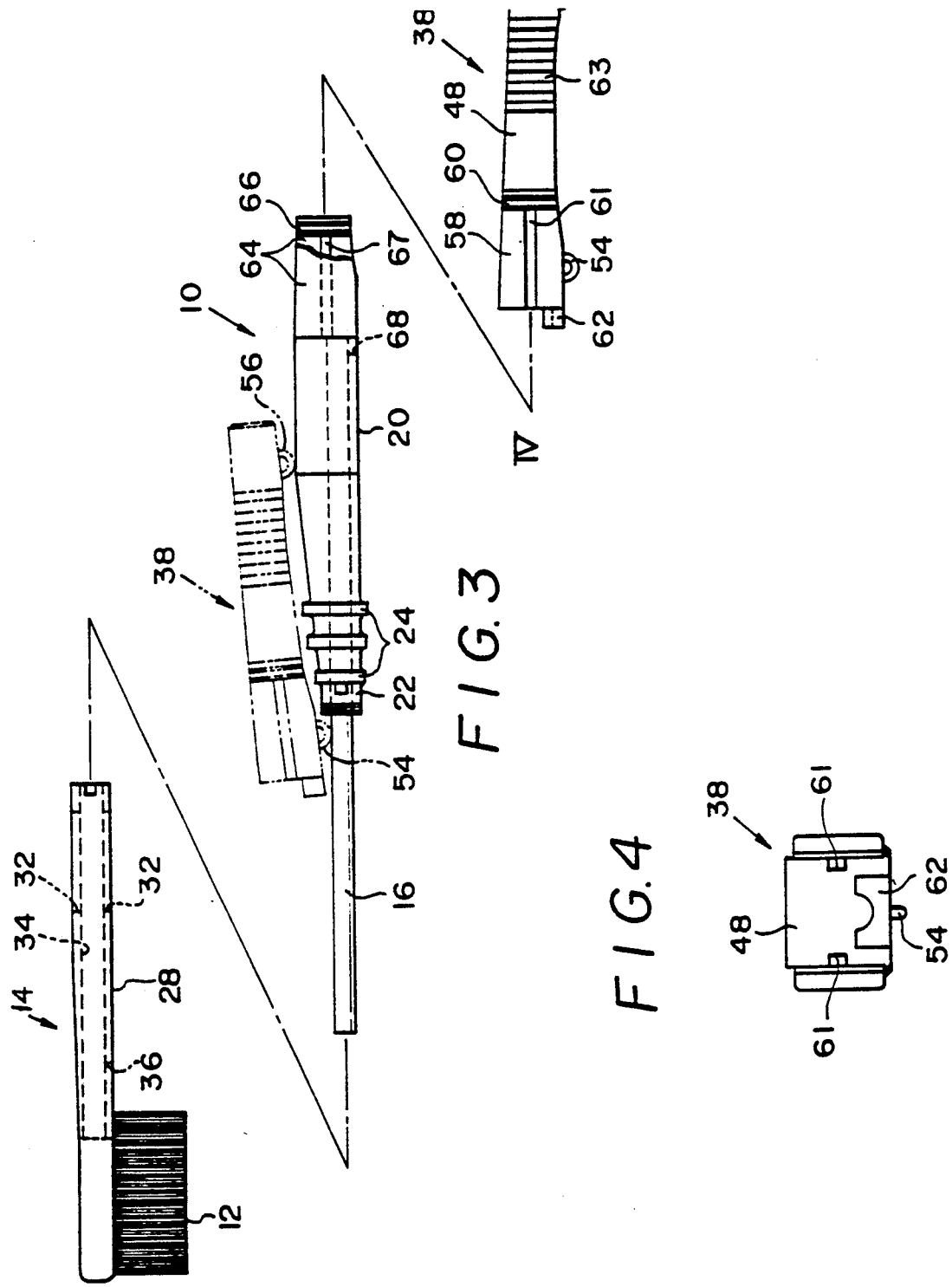

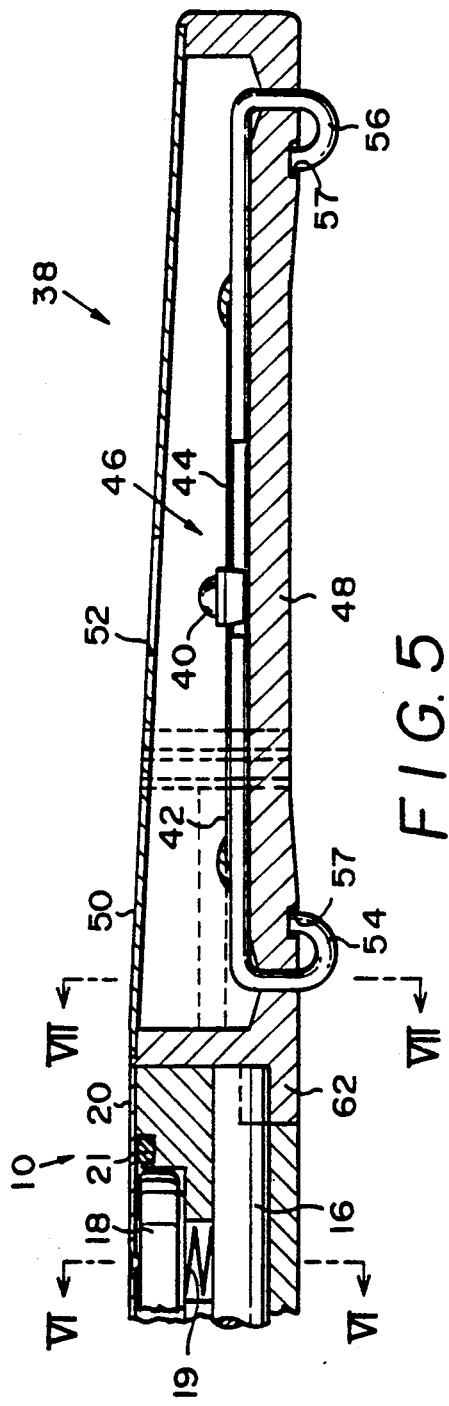
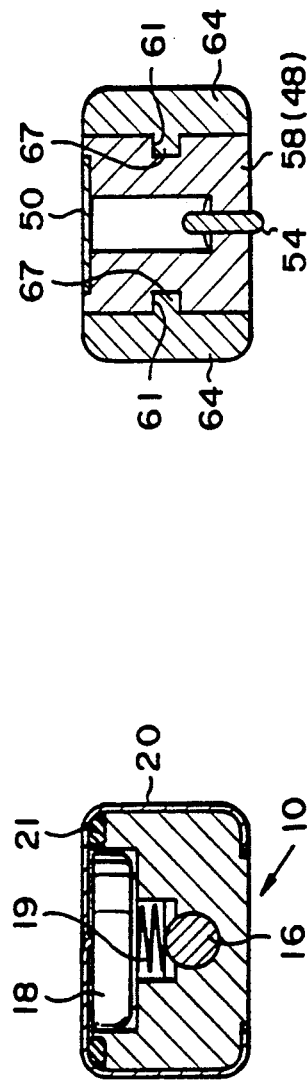

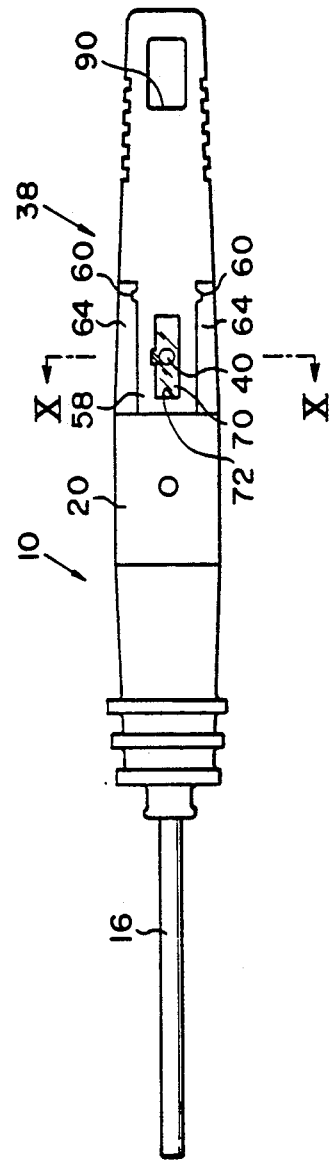
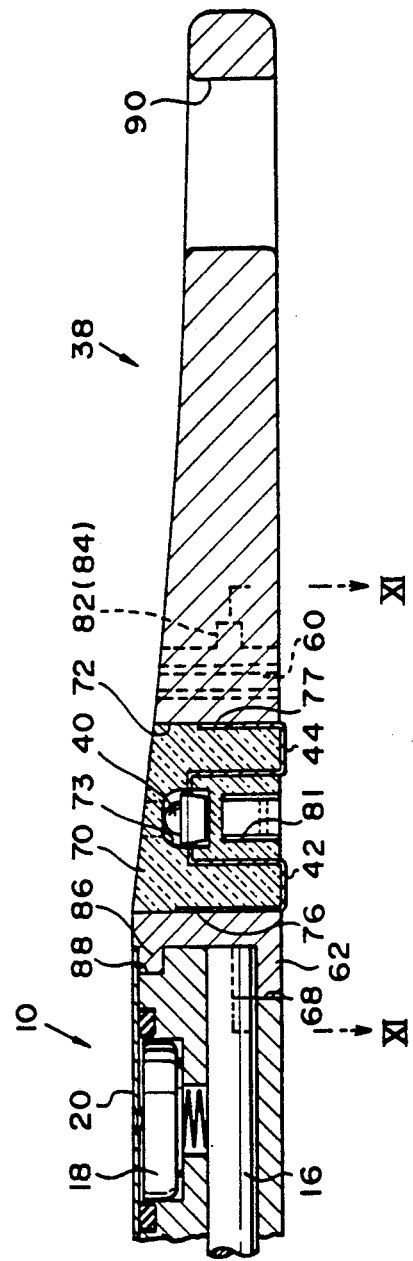
FIG.8
FIG.9

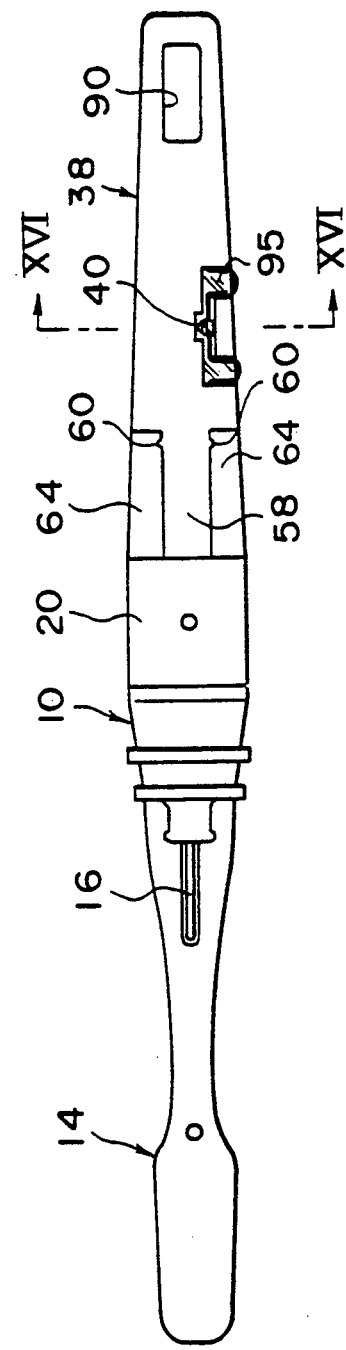

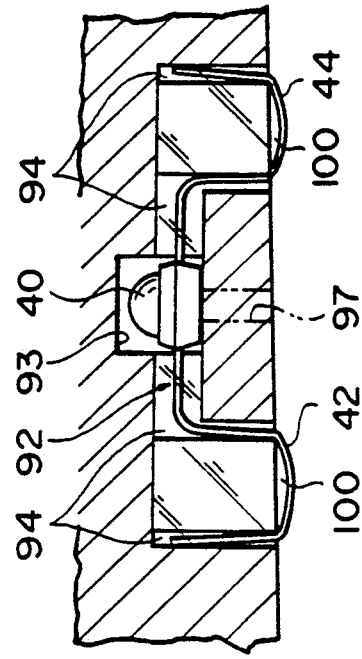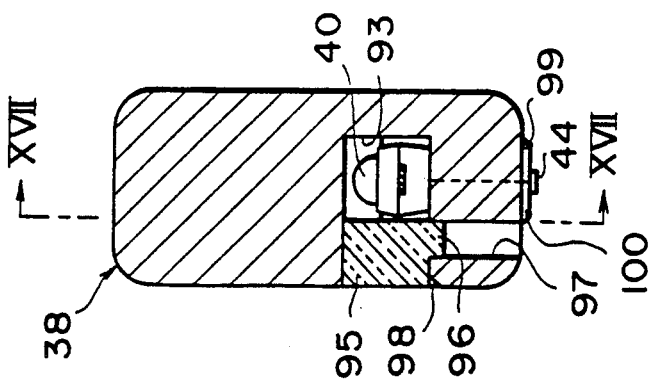

TOOTHBRUSH WITH VOLTAGE TESTER

BACKGROUND OF THE INVENTION

1. Field of the Invention

The present invention relates to an electronic toothbrush and, more specifically, to a combination of an electronic toothbrush for effectively removing bacterial plaque on the teeth by causing electric current to flow between the teeth and the toothbrush, and a tester for detecting the voltage of the electric power source of the toothbrush.

2. Description of the Related Art

Many proposals have hitherto been made on electronic toothbrushes adapted to cause electric current to flow between the teeth and the toothbrush so as to effectively remove bacterial plaque on the teeth and enhance the permeation of fluorides contained in the dentifrice (e.g., Japanese Patent Publication No. 27390/1973, and Japanese Utility Model Publication No. 5092/1968). However, such conventional electronic toothbrushes have failed to successfully come into general use because their complicated structures involve high production costs, and also because they can be handled only with difficulty. In order to overcome these drawbacks, the present applicant has previously proposed an electronic toothbrush, described in Japanese Patent Publication No. 1842/1988.

In order that an electronic toothbrush can properly perform its function, the power source voltage must be maintained at a predetermined value. Therefore, if the electronic toothbrush has a structure in which an electric power source, such as a battery, is disposed in the grip portion of the toothbrush, the voltage of the power source must be checked periodically. For this purpose, the present applicant has previously proposed a voltage tester, described in Japanese Patent Laid-open Publication No. 64968/1987, so that the user will be urged to check the voltage of the built-in power source of an electronic toothbrush periodically by means of the voltage tester.

The voltage tester previously proposed by the present applicant is advantageous in that it can be operated with ease. Thus, this voltage tester is designed to make the operation of checking the voltage of the power source of an electronic toothbrush as simple as possible so that the user will not fail to attend to the operation. However, because the voltage tester is a body separate from the electronic toothbrush, and is an instrument that need not be used at every tooth-brushing, it is necessary for the voltage tester to be stored in a certain place when not in use, and be taken out when necessary. This means that the voltage checking operation can still be troublesome in view of the fact that the users may sometimes even fail to attend to their daily tooth-brushing.

The present applicant has previously made proposals, for example, in Japanese Patent Application No. 133053/1989 (filed on May 26, 1989), on structures where a voltage-detecting function is incorporated in an electronic toothbrush. However, such a structure is rather complicated and involves an increase in the production cost.

SUMMARY OF THE INVENTION

The present invention has been made in view of the above-described points. An object of the present invention is to enable easier checking of the effectiveness of the electric power source disposed in a grip portion of an electronic toothbrush without involving a complicated structure or an increase in the production cost.

According to the present invention, there is provided an electronic toothbrush comprising: a head portion studded with bristles; a grip portion adapted to be gripped manually; an electric power source, one pole of which is connected with an outer surface of the grip portion and the other pole of which is connected with the head portion; and a voltage tester separably coupled with the grip portion, the voltage tester being adapted to be separated from the grip portion and placed onto electric paths from the electric power source for testing the condition of the electric power source.

With the above-specified arrangement, the electronic toothbrush normally incorporates the voltage tester which serves as, for example, a part of the grip portion. When the effectiveness of the electric power source is to be checked, the tester is separated from the grip portion and set at a certain position on the electronic toothbrush.

BRIEF DESCRIPTION OF THE DRAWINGS

FIG. 1 is a plan view of an electronic toothbrush with a voltage tester according to a first embodiment of the present invention;

FIG. 2 is a bottom view of the first embodiment;

FIG. 3 is an exploded front view of the first embodiment;

FIG. 4 is a view taken from the position IV shown in FIG. 3;

FIG. 5 is an enlarged sectional view of the essential parts of the first embodiment;

FIG. 6 is a sectional view taken along the line VI—VI shown in FIG. 5;

FIG. 7 is a sectional view taken along the line VII—VII shown in FIG. 5;

FIG. 8 is a plan view of a second embodiment of the present invention, the embodiment being shown with a head portion thereof omitted;

FIG. 9 is an enlarged sectional view of the essential parts of the second embodiment;

FIG. 15 is a plan view of a third embodiment of the present invention;

FIG. 16 is an enlarged sectional view taken along the line XVI—XVI shown in FIG. 15;

FIG. 17 is a sectional view taken along the line XVII—XVII shown in FIG. 16;

DESCRIPTION OF THE PREFERRED EMBODIMENTS

Figure 10:
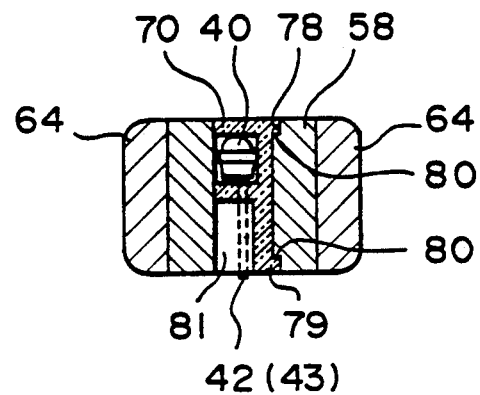
FIG. 10 is a sectional view taken along the line X—X shown in FIG. 8.
Figure 11:
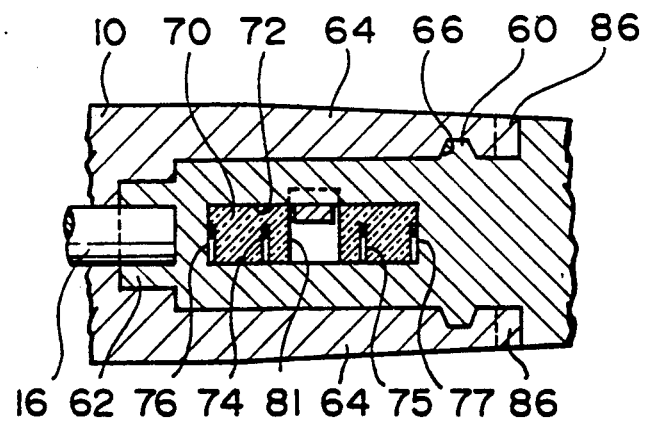
FIG. 11 is a sectional view taken along the line XI—XI shown in FIG. 9.

The present invention will now be described with respect to the preferred embodiments thereof which are shown in the drawings.

FIGS. 1 through 7 show a first embodiment of the present invention. A toothbrush according to this embodiment has an arrangement whereby it functions as an electronic toothbrush, which arrangement is substantially the same as that of the electronic toothbrush disclosed in Japanese Patent Publication No. 1842/1988 or U.S. Pat. No. 4,726,806. Specifically, the electronic toothbrush mainly comprises a grip portion 10 adapted to be gripped by the user, and a head portion 14 studded with bristles 12, the head portion 14 forming a unit different from the grip portion 10 and being separably mounted thereon. The grip portion 10 has a main body along the axis of which a bar 16 made of an electrically conductive material extends, with a part of the bar 16 projecting from a forward end of the main body, and the remaining part of the bar 16 extending into the main body. A battery 18 is disposed in the main body of the grip portion 10 and in the vicinity of a rearward portion of the bar 16. The conductive bar 16 is connected via a coil spring 19 with one pole, e.g., the negative pole, of the battery 18. A conductive plate 20, which is made of an electrically conductive material and defines an outer surface of the grip portion 10, is connected with the other pole of the battery 18, e.g., the positive pole. The grip portion 10 further has a sealing member 21, a coupling projection 22 for mounting the head portion 14 on the grip portion 10, and flanges 24 for draining off water.

The head portion 14 basically comprises a head 26 studded with the bristles 12, and a shank 28 integral with the head 26. The rearward end portion of the shank 28, which is on the right side as viewed in FIGS. 3, has a coupling recess 30 formed in the center thereof. The coupling recess 30 is engageable with the coupling projection 22 of the grip portion 10, so that the head portion 14 can be mounted on the grip portion 10 with snug fit. The head portion 14 further comprises a pair of slits 32 each axially extending from the bottom of the coupling recess 30 to a substantially middle position of the shank 28, and opening into the top or bottom surface of the shank 28.

The shank 28 has a bar inserting portion 34 formed along the axis thereof, the portion 34 extending from the rearward end of the shank 28, i.e., from the bottom of the coupling recess 30, to a position close to the rearward end of the bristles 12. When the head portion 14 is mounted on the grip portion 10, as shown in FIGS. 1 and 2, the inserting portion 34 receives that part of the conductive bar 16 projecting from the grip portion 10. The bar 16 and the portion 34 have their dimensions set in such a manner that, when that part of the bar 16 is received by the portion 34, the forward end of the bar 16 is at the bottom of the inserting portion 34. Since the slits 32 communicate with the bar inserting portion 34, the part of the bar 16 received in the portion 34 is exposed to the outside through the slits 32. A communication groove 36 serves as a part of a liquid passage for electrically connecting the bar 16 partially received in the portion 34 with the bristles 12 via a liquid such as saliva. The communication groove 36 axially extends through a predetermined length from the vicinity of the bristles 12 to communicate with the bar inserting portion 34. Small grooves 37 extend from the surface of the communication groove 36 toward the root of the bristles 12 so as to make sure the electrical connection between the bristles 12 and the conductive bar 16 via saliva, etc.

In this embodiment, the electronic toothbrush having the above-described arrangement has a tester 38 for checking the effectiveness of the battery 18 which tester is separably and coaxially coupled with the rearward end of the grip portion 10.

As shown in detail in FIG. 5, the tester 38 includes, for the above-stated purpose, a light emitting body 46 comprising a light emitting diode 40, and a pair of terminals 42 and 44 extending substantially symmetrically from the diode 40, the light emitting body 46 being accommodated in a tester body 48 forming an elongated casing. The tester body 48 opens upward, as viewed in FIG. 5, and the opening is covered with a cover 50. The cover 50 is formed with a window 52 at a position opposing the light emitting diode 40 so that the light emitting diode 40 can be visually observed from above. A pair of contact terminals 54 and 56 partially project from the bottom of the body 48 and from positions close to the longitudinal ends of the body 48, each of the terminals 54 and 56 continuously extending into the tester body 48 to be positively connected with the terminals 42 and 44 of the light emitting body 46, respectively, by soldering or the like. Those portions of the contact terminals 54 and 56 which project from the body 48 are curved into a substantially U-like shape, with their distal ends being received in a pair of recesses 57 formed on the bottom surface of the body 48.

The forward end portion of the tester body 48, i.e., the end portion on the side of the grip portion 10, is formed with a reduced width, and is adapted to serve as a coupling projection 58, described later, which can be coupled with the grip portion 10. The coupling projection 58 has, on its side surfaces, engagement projections 60 and guide grooves 61. The coupling projection 58 also has, at a lower position on the forward end face thereof, a projection piece 62 which has its upper surface portion cut into a semicircular shape (as best shown in FIG. 4) so as to be engageable with a lower position at the rearward end of the bar 16 within the grip portion 10. The tester 38 further includes a plurality of recesses and projections 63 which, when they are gripped during the mounting and dismounting of the tester 38 onto and from the grip portion 10, serve to prevent slip of hand.

On the other hand, the rearward end portion of the grip portion 10 has a pair of wall-shaped holding arms 64 which project rearward from positions at the rearward end of the conductive plate 20. Formed on the inner walls of the holding arms 64 are engagement recesses 66 corresponding to the engagement projections 60 of the coupling projection 58, and guide ridges 67 corresponding to the guide grooves 61 and extending axially to provide the function of preventing rotation of the tester 38 relative to the grip portion 10. A notch 68 is formed at a lower portion of the main body of the grip portion 10 to correspond to the projection piece 62 of the coupling projection 58. Accordingly, when the tester 38 is not mounted on the grip portion 10, the lower portion at the rearward end of the conductive bar 16 is exposed to the outside.

The tester 38 in its dismounted state, shown in FIG. 3, is coupled with the rearward end of the grip portion 10 in the following manner. The guide ridges 67 on the holding arms 64 of the grip portion 10 are aligned with the corresponding guide grooves 61 on the coupling projection 58 of the tester 38 and, thereafter, the tester 38 is pushed forward. This pushing causes the engagement projections 60 on the side surfaces of the coupling projection 58 to push the holding arms 64 away from each other, then resiliently fit into the engagement recesses 66 on the inner walls of the arms 64. At this time, the projection piece 62 of the coupling portion 58 fits into the notch 68. In this way, the tester 38 is coupled with the grip portion 10 by snug fits. Further, the lower portion at the rearward end of the conductive bar 16, which has previously been exposed, is covered with the projection piece 62. Conversely, when the tester 38 is to be separated from the grip portion 10, a portion of the tester 38 including the recesses and projections 63 are gripped, and the tester 38 is pulled rearward.

With this embodiment having the above-described construction, when the tester 38 is coupled with the grip portion 10, the tester 38 functions as a part of the grip portion 10. The tester 38 in its coupled state may be used during tooth-brushing, stored, or carried. When it is necessary to check the effectiveness of the battery 18, the tester 38 is separated from the grip portion 10, then set at a position such as that indicated by two-dot chain lines in FIG. 3. In this position of the tester 38, the contact terminal 54 contacts the conductive bar 16 while the other contact terminal 56 contacts the conductive plate 20. If the battery 18 is effective, the light emitting diode 40 of the light emitting body 46 is supplied with electricity, and emits light. The emission of light is confirmed through the window 52 on the cover 50 of the tester 38.

Although in FIG. 3, the head portion 14 is drawn as being separated from the grip portion 14 when the contact terminal 54 of the tester 38 is brought into contact with the bar 16, the separation of the head portion 14 is not always necessary to the checking of the effectiveness of the voltage because the slits 32 are formed on the head portion 14.

FIGS. 8 to 14 show another embodiment of the present invention. In these drawings, component parts which are the same as or correspond to those of the foregoing embodiment are designated by the identical reference numerals, and the descriptions of these component parts will be omitted. The main difference of the second embodiment from the first embodiment is that a tester 38 includes a holding member 70 holding a light emitting body 46 and being made of a transparent material. The holding member 70 with the light emitting body 46 is fit into a mounting hole 72 formed in a body of the tester 38.

More specifically, the holding member 70 is, as a whole, a thin-plate-shaped member, and is formed with a recess 73 into which a light emitting diode 40 of the light emitting body 46 is inserted from one side of the member 70, grooves 74 and 75 respectively receiving proximal end portions of terminals 42 and 44 extending from the light emitting diode 40, and thin-walled portions 76 and 77 defining gaps on a first pair of opposing side walls of the member 70 where distal end portions of the terminals 42 and 44 are, after being bent, respectively received between the side walls and the mated inner walls of the mounting hole 72 of the tester body. In order to prevent dropping off of the holding member 70 from the mounting hole 72, one of the second pair of opposing side walls of the member 70 has a projection piece 78 at an upper position, as viewed in FIG. 10, and an engagement projection 79 at a lower position. On the other hand, the mounting hole 72 includes upper and lower engagement stepped portions 80 formed in correspondence with the projection piece 78 and the engagement projection 79. The light emitting body 46 is assembled onto the holding member 70, and the resultant assembly is mounted into the mounting hole 72 in the following manner. The light emitting diode 40 is inserted into the recess 73 of the holding member 70, and the terminals 42 and 44 are respectively inserted through the grooves 74 and 75 until parts of the terminals 42 and 44 project from the lower surface (as viewed in FIG. 9) of the holding member 70. These parts of the terminals 42 and 44, which project downward in this state, are bent outward along the lower surface of the member 70 and maintained in their bent state. The holding member 70 with the light emitting body 46 is inserted into the mounting hole 72 of the tester body from above, as viewed in FIGS. 9 and 10, and the mounting is completed when the engagement projection 79 engages with the lower engagement stepped portion 80. The projection piece 78 engages with the upper engagement stepped portion 80 to serve as a stopper. When the holding member 70 is being inserted into the mounting hole 72, the terminals 42 and 44 have their distal end portions pushed by the inner walls of the hole 72 and are curved into a U-like-shape, resulting in the distal end portions of the terminals 42 and 44 being respectively received in the thin-walled portions 76 and 77 (see FIG. 9). The height of the holding member 70 is such that, when the upper surface of the member 70 is flush with the adjacent surfaces of the tester body, the substantially intermediate portions of the terminals 42 and 44 project from the bottom surface of the tester 38 by a dimension corresponding to their diameter or thickness. A hole 81 is further cut in the holding member 70 to thereby reduce the thickness of that part of the holding member 70 provided with the engagement projection 79 so that, during the insertion of the member 70, the projection-provided part of the member 70 can deform inward and then resiliently engage with the associated stepped portion 80 with snug fit.

The second embodiment has arrangements for preventing the tester 38 from undergoing rotation relative to a grip portion 10 and from dropping off therefrom, the arrangements being different from those of the first embodiment. Specifically, the grip portion 10 includes a pair of holding arms 64 having, at their rearward ends, rearwardly projecting engagement projections 82, while the tester 38 includes a pair of engagement recesses 84 corresponding to the projections 82. Further, the tester 38 has, at an upper position on the forward end face thereof, an engagement projection 86, while the main body of the grip portion 10 has, on its rearward end face and, particularly, on a certain part of the upper surface defined by the conductive plate 20, an engagement recess 88.

The tester 38 further includes a through hole 90 formed in a rearward end portion of the tester body, and the hole 90 may be used to suspend the electronic toothbrush from a hook or the like (not shown).

Figure 12:
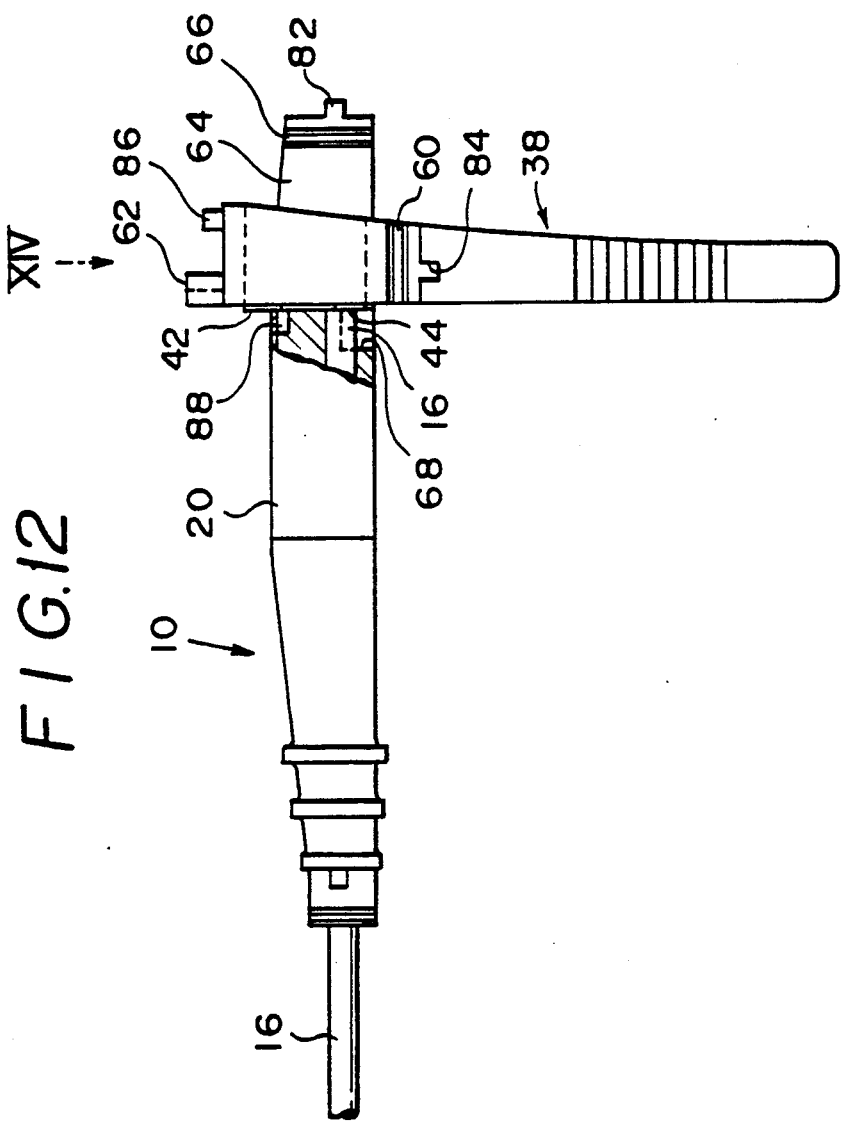
FIG. 12 is a fragmentary, partially cut-away front view of the second embodiment, showing the state where the effectiveness of the voltage is checked.
Figure 13:
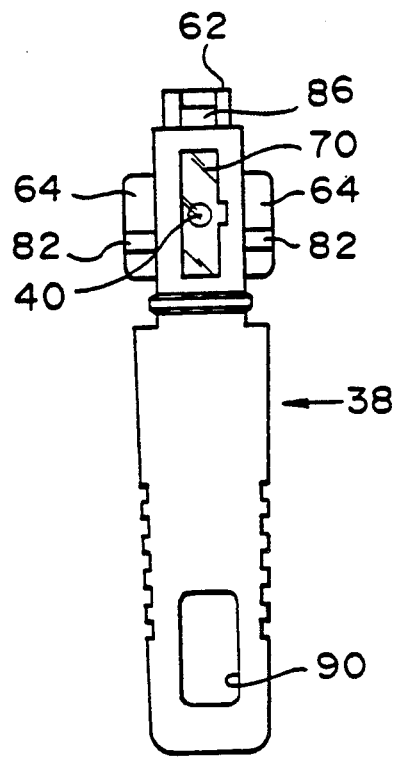
FIG. 13 is a right side view (as viewed in FIG. 12) of the second embodiment in the state of FIG. 12.
Figure 14:
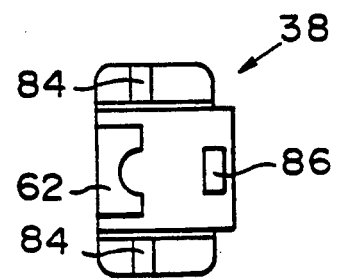
FIG. 14 is a view taken from the position XIV shown in FIG. 12.
Figure 18:
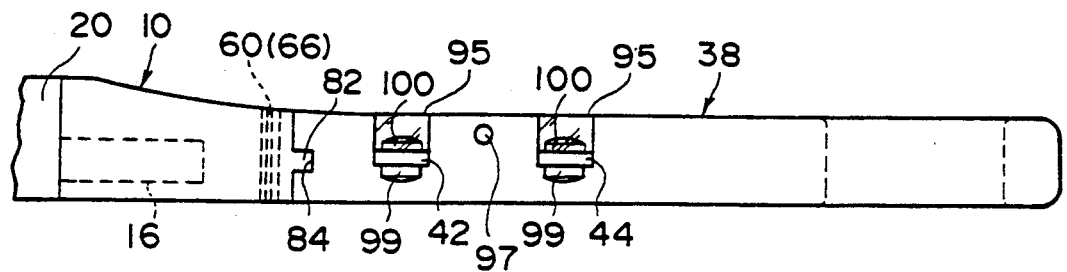
FIG. 18 is a fragmentary, enlarged front view of the third embodiment.

Also in this embodiment, the tester 38 is separably coupled, at its coupling projection 58 at the forward end, with the pair of holding arms 64 of the grip portion 10, and the tester 38 normally functions as a part of the grip portion 10. When the effectiveness of the battery 18 is to be checked, the tester 38 is, as shown in FIGS. 12 and 13, dismounted from the grip portion 10, and swung, with its coupling projection 58 being positioned between the holding arms 64, substantially through 90 degrees from the position at which the tester 38 is coupled, until the terminals 42 and 44 of the light emitting body 46, which project from the tester 38, contact the rearward ends of the conductive plate 20 and the conductive bar 16, respectively. At this time, the engagement recess 88 and a notch 68, both provided in the grip portion 10, respectively cause a part of the rearward end of the conductive plate 20 and a part of the rearward end of the conductive bar 16 to be exposed rearward, thereby assuring positive electrical connection of these parts with the corresponding terminals of the light emitting body 46.

According to this embodiment, since the terminals 42 and 44 per se of the light emitting body 46 can function as contact terminals, there is no need to provide, as separate members, the wire-like contact terminals 54 and 56 of the previous embodiment. Accordingly, the soldering of the contact terminals with the terminals extending from the light emitting diode, and other associated operations will also be unnecessary Therefore, when the second embodiment is compared with the first embodiment, the former requires a smaller number of component parts, which is advantageous in simplifying the manufacture of the electronic toothbrush, and in reducing the production cost.

According to each of the foregoing embodiments, the head portion 14, the grip portion 10 and the tester 38 of the toothbrush are separable from each other. Accordingly, when these are separated, the toothbrush is very compact, and can be carried conveniently during travel, etc.

The conductive bar 16 of each of the above-described embodiments is integrated with the grip portion 10 during the fabrication of the portion 10. Conventionally, it has been necessary, during the fabrication, to form a hole where a pin is passed to support the bar 16 at a predetermined position. This results in that the hole remains in the main body of the grip portion 10 after the completion of the fabrication, leading to a problem in which the remaining hole might act as an inlet through which water can enter to reach the battery disposed in the main body of the grip portion 10. In contrast, in the above-described embodiments, since the notch 68 is provided to allow a lower part of the conductive bar 16 at the rearward end thereof to be exposed, it is possible to fabricate the grip portion 10 by utilizing the notch 68 to set a structure for supporting the bar 16, thereby eliminating the need to form the above-described pin hole. This in turn eliminates the risk of the battery being damaged, while facilitating the fabrication of the grip portion 10.

FIGS. 15 through 20 show still another embodiment of the present invention. Descriptions will be given concentrating on the differences of the third embodiment from the second embodiment illustrated in FIGS. 8 through 14.

Figure 20:
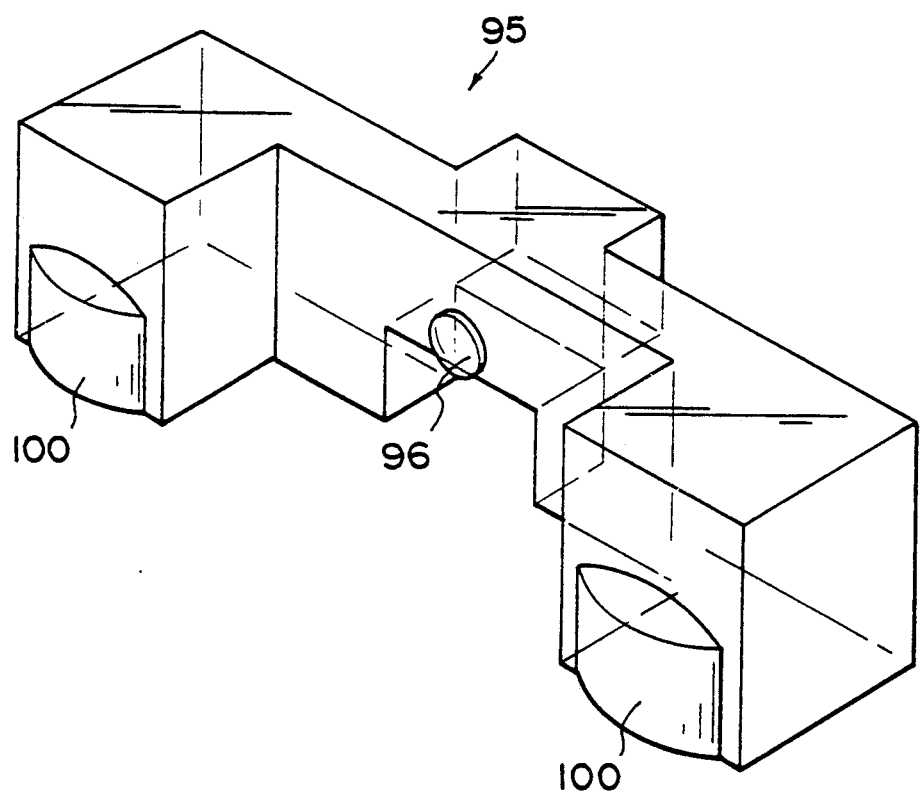
FIG. 20 is an enlarged perspective view of a cover used in the third embodiment.

A tester 38 has a recess portion 92 which is, as shown in FIGS. 15 and 17, gate-shaped on the whole, and is formed at a corner between the front surface and an adjacent side surface of the tester body. The recess portion 92 receives a light emitting diode 40, and parts of a pair of terminals 42 and 44 extending from the diode 40, the terminals 42 and 44 being curved with their intermediate portions exposed on the front surface of the tester body. The recess portion 92 includes a recess 93 for receiving the light emitting diode 40, and grooves 94 for guiding the terminals 42 and 44 in a generally U-shaped shape. The recess portion 92 of the tester 38 which thus receives a light emitting body 46 is covered with a cover 95 made of a transparent material and disposed over the recess portion 92. As shown in FIG. 20, the cover 95 is generally gate-shaped, and it defines a part of the outer periphery of the tester 38 by covering the recess portion 92. The cover 95 has a projection 96 formed in the center thereof, while the tester body has an engagement hole 97 formed in correspondence with the projection 96. Accordingly, when the cover 95 is disposed over the recess portion 92, the projection 96 fits into the engagement hole 97 to prevent dropping off of the cover 95. Denoted by reference numeral 98 in FIG. 16 is a slope portion for guiding the cover 95 when it is being mounted. Thick-walled portions 100 and 99 are respectively formed on certain surfaces of the cover 95 and the recess-92-formed portion of the tester body, the portions 99 and 100 cooperating with each other to guide those portions of the terminals 42 and 44 exposed on the front surface of the tester body in such a manner that the exposed terminal portions project slightly from that front surface.

Figure 19:
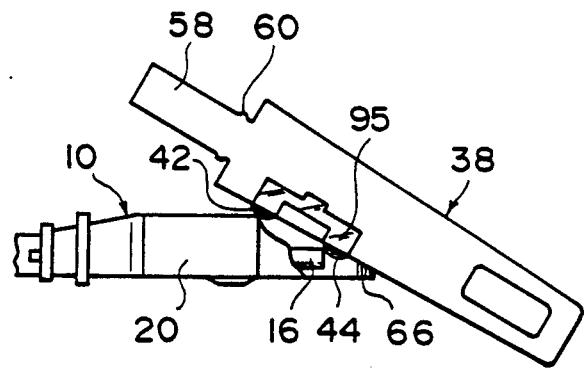
FIG. 19 is a fragmentary, partially cut-away front view of the third embodiment, showing the state where the effectiveness of the voltage is checked.

In this embodiment, when the effectiveness of the battery is to be determined, the tester 38 is separated from the grip portion 10, then, as shown in FIG. 19, the tester 38 is rotated about its longitudinal axis about 90 degrees until the terminal 44 contacts a rearward end portion of the conductive bar 16 while the terminal 42 contacts a rearward end portion of the conductive plate 20. The operation with this arrangement is advantageous in that both the contact conditions of the terminals and the light-emitting condition of the diode 40 can be confirmed at a glance, and that the exposed portions of the terminals which also project can be brought into contact with ease. The voltage checking operation is further facilitated particularly if, as shown in FIG. 19, the dimensions of the relevant members are set in such a manner that, when the projecting curved portion of the terminal 44 rests on a rearward end portion of the conductive bar 16, the terminal 42 comes into contact with a rearward end portion of the plate 20. When this embodiment is compared with the above-described second embodiment, the former is advantageous in that: there is no need to form holes such as the mounting hole in the tester 38; the volume of the cover made of a transparent material can be reduced; and the assembly of the light emitting diode 40 and the mounting of the cover 95 are easier. As a result, the electronic toothbrush according to the third embodiment can be manufactured at low cost, while assuring a more positive voltage-checking operation. In addition, since the light emitting diode 40 and the cover 95 are positioned at the corner portion of the tester 38, the tester 38 has to be cut or notched only by a small volume, thereby assuring a greater strength of the tester 38.

Also in the third embodiment, parts of the terminals 42 and 44 are exposed at locations where the toothbrush is most possibly gripped by the user. Therefore, whenever the user's hand touches the exposed portions of the terminals during tooth-brushing or the like, foreign matter that may be adhered to the terminals can be removed therefrom, thereby enabling electrical connection to be maintained at good conditions.

Although in the foregoing embodiments, the tester 38 includes a light emitting diode, the arrangement that can be adopted is not limited thereto but may be any other construction so long as the effectiveness of the voltage can be checked.

As has been described above, according to the present invention, since the tester is separably coupled with the grip portion of the electronic toothbrush, this provides excellent advantages. The tester can serve as a part of the grip portion during tooth-brushing, thereby eliminating the need to separately prepare a place to store the tester. On the other hand, when checking is required, the tester can be separated and used to easily check the effectiveness of the power source voltage.

What is claimed is:

1. An electronic toothbrush comprising:
   a head portion studded with bristles;
   a grip portion adapted to be gripped manually;
   an electric power source, one pole of which is connected with an outer surface of said grip portion and other pole of which is connected with said head portion; and
   a voltage tester including a tester body for supporting all other testing components of said tester, said entire tester body defining a part of said grip portion that is manually gripped when attached to said grip portion when not being used for testing purposes and separating therefrom for testing the condition of said electric power source.

2. An electronic toothbrush according to claim 1, wherein said electric power source is a battery disposed in said grip portion.

3. An electronic toothbrush according to claim 1, further comprising mutually interengageable coupling means on both said grip portion and said voltage tester for separably attaching said voltage tester to said grip portion.

4. An electronic toothbrush according to claim 1, wherein said
   tester body defines an end portion of said toothbrush when said tester body is coupled to the end of said grip portion, and said body supports
   a light emitting member mounted inside said tester body and being visible from outside said tester body; and
   a pair of electrical conductors extending from said light emitting member and exposed at least partially form said tester body.

5. An electronic toothbrush according to claim 4, wherein said electric power source is disposed within said grip portion, and said grip portion comprises a first electrically conductive member mounted on the exterior of said grip portion and being electrically connected to one pole of said electric power source, and a second electrically conductive member in the form of a conductive bar extending lengthwise along said grip portion between said bristles at one end and being electrically connected to the other pole of said electric power source at the other end, a portion of said bar extending outside of the grip portion,
   whereby when said pair of exposed electrical conductors of said voltage tester touch said electrically conductive member and said exposed portion of said bar, the emission of light by said light emitting member is determined by the condition of the electric power source.

6. An electronic toothbrush according to claim 1, wherein said head portion is separable from said grip portion.

7. An electronic toothbrush comprising:
   a head portion at one end of the toothbrush, said head portion studded with bristles;
   a grip portion in the middle of the toothbrush, said grip portion containing a battery in the interior thereof, said grip portion comprising: a first electrically conductive member to be touched by a user at least when brushing and being electrically connected to one pole of said battery; and a second electrically conductive member to be electrically connected to said bristles of said head portion at least when brushing and being electrically connected to the other pole of said battery; and
   a voltage tester defining an end part of said grip portion when not in use for testing purposes and being separable therefrom for testing the condition of said electric power source, said tester comprising; a tester body having coupling means associated with said grip portion for separably coupling said tester body with said grip portion; a light emitting member inside said tester body and being visible from outside said tester body; and a pair of electrical conductors extending from said light emitting member and exposed at least partially form said tester body;
   whereby when said pair of electrical conductors of said tester separated form said grip portion touch said first and second conductive members of said grip portion, the emission of light by said light emitting member is determined by the condition of the battery.

8. An electronic toothbrush according to claim 7, wherein said first electrically conductive member is mounted on the exterior of said grip portion, and said second electrically conductive member extends lengthwise from adjacent said battery to adjacent said bristles.

9. An electronic toothbrush according to claim 8, wherein a portion of said second electrically conductive member is exposed to the exterior of said head portion.

10. An electronic toothbrush according to claim 9, wherein said exposed pair of electrical conductors of said voltage tester are disposed at locations corresponding to the locations of said first electrically conductive member and said exposed second electrically conductive member, so that when said tester body is placed in a predetermined portion on said grip portion, said exposed pair of electrical conductors of said voltage tester can simultaneously touch said first and second electrically conductive members.

11. An electronic toothbrush according to claim 7, wherein said coupling means comprises:
    a fork of two arms on the end of said grip portion opposing said tester body, said arms being openable outwardly and normally having a resilient tendency to inward closure; and
    a boss on the end of said tester body opposing said arms, said boss being fitted in a recess between said arms.

12. An electronic toothbrush according to claim 11, wherein said tester body has a through hole, and a transparent holding member holding said light emitting member and said pair of electrical conductors is fitted in said through hole.

13. An electronic toothbrush according to claim 12, wherein said transparent holding member is disposed in said boss of said tester body.

14. An electronic toothbrush according to claim 13, wherein when said voltage tester is separated from said grip portion, a portion of the edge of said first electrically conductive member and the end of the said second electrically conductive member are exposed, and wherein locations of said exposed pair of electrical conductors of said tester correspond to the locations of said exposed edge of said first electrically conductive member and said exposed end of said second electrically conductive member, so that when said tester is turned substantially perpendicularly to the length of said grip portion within said arms, said exposed pair of electrical conductors of said tester can simultaneously touch said exposed first and second electrically conductive members.

15. An electronic toothbrush according to claim 11, wherein said tester body has a recess at the side corner thereof, and said light emitting member and said pair of electrical conductors are disposed in said recess while a portion of said electrical conductors are exposed outside said tester body, and wherein a transparent cover is fitted onto said recess.

16. An electronic toothbrush according to claim 15, wherein when said voltage tester is separated from said grip portion, a portion of the edge of said first electrically conductive member and the end of said second electrically conductive member are exposed, and wherein locations of said exposed pair of electrical conductors of said tester correspond to the locations of said exposed edge of said first electrically conductive member and said exposed end of said second electrically conductive member, so that when said tester is turned substantially perpendicularly around the longitudinal axis of said tester within said arms, said exposed pair of electrical conductors of said tester can simultaneously touch said exposed first and second electrically conductive members.

17. An electronic toothbrush according to claim 7, wherein said tester body has a recess extending lengthwise thereof and said light emitting member is disposed within said recess, said tester body further having a closure for closing said recess, said closure having an opening through which said light emitting member is visible from outside said tester body.

18. An electronic toothbrush according to claim 17, wherein each of said electrical conductors is connected to a conductor bar penetrating a wall of said tester body to outside said tester body.

* * * * *